(12) United States Patent
Seeley et al.

(10) Patent No.: US 9,279,181 B2
(45) Date of Patent: Mar. 8, 2016

(54) FLUIDIZED BED PYROCARBON COATING

(75) Inventors: Mark E. Seeley, Austin, TX (US); Fletcher Derek Southard, Austin, TX (US); Mike James Mewhort, Pflugerville, TX (US); Joseph Earl Robinson, Pflugerville, TX (US); Roger William Leikam, Round Rock, TX (US); Jeff Wayne Stark, Round Rock, TX (US); Brett A. Bickerton, Austin, TX (US); Jonathan C. Stupka, Austin, TX (US); David Wilde, Georgetown, TX (US); Cephas M. Wozencraft, Austin, TX (US)

(73) Assignee: On-X Life Technologies, Inc., Austin, TX (US)

( * ) Notice: Subject to any disclaimer, the term of this patent is extended or adjusted under 35 U.S.C. 154(b) by 1369 days.

(21) Appl. No.: 13/032,213

(22) Filed: Feb. 22, 2011
(Under 37 CFR 1.47)

(65) Prior Publication Data

US 2011/0311714 A1    Dec. 22, 2011

Related U.S. Application Data

(60) Provisional application No. 61/306,819, filed on Feb. 22, 2010.

(51) Int. Cl.
*B23P 15/26* (2006.01)
*C23C 16/26* (2006.01)
*A61L 27/30* (2006.01)
*C23C 16/442* (2006.01)
*C23C 16/458* (2006.01)

(Continued)

(52) U.S. Cl.
CPC ............... *C23C 16/26* (2013.01); *A61L 27/303* (2013.01); *C23C 16/442* (2013.01); *C23C 16/458* (2013.01); *B05D 1/22* (2013.01); *B05D 1/60* (2013.01)

(58) Field of Classification Search
CPC ........ B23P 19/04; B23P 19/046; B23Q 3/103
See application file for complete search history.

(56) References Cited

U.S. PATENT DOCUMENTS

| 4,444,811 A | 4/1984 | Hsu et al. |
| 4,474,122 A | 10/1984 | Hokari et al. |
| 4,486,473 A | 12/1984 | Kaae et al. |

(Continued)

FOREIGN PATENT DOCUMENTS

| EP | 0252480 A2 | 1/1988 |
| EP | 0546756 A2 | 6/1993 |

OTHER PUBLICATIONS

Patent Cooperation Treaty, International Search Report mailed Nov. 24, 2011 in International application No. PCT/US2011/025758.

(Continued)

*Primary Examiner* — Lee D Wilson
(74) *Attorney, Agent, or Firm* — Trop, Pruner & Hu, P.C.

(57) ABSTRACT

Arrangements are provided for assembling multiple substrates for coating within a fluidized bed coater so as to deposit a coating of uniform thickness across the entire exterior surface thereof. One embodiment includes a method for coating orthopedic implants having convex and concave surfaces with pyrocarbon by pyrolytic decomposition of a hydrocarbon.

14 Claims, 9 Drawing Sheets

(51) Int. Cl.
*B05D 1/22* (2006.01)
*B05D 1/00* (2006.01)

(56) References Cited

U.S. PATENT DOCUMENTS

| | | | |
|---|---|---|---|
| 5,284,676 A * | 2/1994 | Accuntius | B01J 8/1809 427/213 |
| 5,514,410 A * | 5/1996 | Ely | A61L 27/303 427/2.24 |
| 5,891,517 A | 4/1999 | Cox | |
| 6,274,191 B1 * | 8/2001 | Emken | B01J 8/1809 427/213 |
| 6,410,087 B1 * | 6/2002 | Wilde | C23C 16/442 427/2.15 |
| 6,596,084 B1 | 7/2003 | Patke | |
| 6,777,029 B2 | 8/2004 | Carnagey, Sr. et al. | |
| 2001/0022988 A1 | 9/2001 | Schwarz et al. | |
| 2007/0041795 A1 | 2/2007 | Neto et al. | |
| 2011/0311714 A1 * | 12/2011 | Seeley | A61L 27/303 427/2.25 |

OTHER PUBLICATIONS

Patent Cooperation Treaty, Written Opinion of the International Searching Authority mailed Nov. 24, 2011 in International application No. PCT/US2011/025758.

Supplementary European Search Report for PCT/US2011/02578 mailed Mar. 14, 2014.

* cited by examiner

FLUIDIZED BED PYROCARBON COATING

This application claims priority to U.S. Provisional Patent Application No. 61/306,819 filed on Feb. 22, 2010 entitled FLUIDIZED BED PYROCARBON COATING, which is hereby incorporated by reference.

BACKGROUND

Pyrolytic carbon, which is referred to herein as pyrocarbon, is generally deposited by thermally decomposing a gaseous hydrocarbon (or other carbonaceous substance) in vapor form as a coating upon relatively small substrates that can be levitated in a fluidized bed along with an ancillary charge of small particles. In the time that has passed since the development of fluidized bed technology for applying pyrolytic carbon coatings, as exemplified for example in U.S. Pat. No. 3,977,896 to Bokros et al. entitled "Process for Depositing Pyrocarbon Coatings", it has been discovered that there are many variables with respect to the fluidized bed environment that may determine the structure of the pyrocarbon that is deposited. Because pyrocarbon (having a microstructure that is free of growth features) is generally deposited when the relative amount of deposition surface area to volume in a fluidized bed is fairly high, such small objects to be coated with pyrocarbon may be tumbled in a bed of minute particles. In many cases, the substrates being coated, which are larger than the minute particles, will exhibit substantially random motion within the fluidized bed. As a result, the surface area of the substrate will generally be substantially equally exposed to the upward flow of the mixture of hydrocarbon and inert gas flowing through the coating enclosure. Consequently all or most surfaces will receive a substantially uniform thickness of pyrocarbon. However, when such relative uniformity of tumbling motion does not occur, possibly because of the particular geometry of the substrates being coated, uniformity of coating thickness may not be achieved.

Specifically, the configurations of some objects or substrates have a tendency to assume a relatively stable orientation in an upwardly flowing fluidized bed despite collisions with other substrates and the particles in the bed. This tendency is referred to as a tendency to "plum-bob" (i.e., to float in one particular orientation within the bed, and not randomly tumble). When such plum-bobbing occurs, an inadequate coating thickness may be applied to surface regions that are essentially shielded or hidden from direct contact with the upwardly moving hydrocarbon stream and "free carbon". This may be because the shielded surface regions experience pyrolysis and deposition of pyrocarbon at a slower rate. The result of such a situation can be an unacceptably thin deposition of pyrocarbon coating in these regions and therefore overall non-uniformity of pyrocarbon thickness across the entire surface of the substrate. For instance, a thin hemispherical shell with a stem protruding axially from within the concave surface (e.g., an orthopedic implant) may float within the coating bed with the convex face facing downward receiving a desired amount of coating while the base of the stem (where it affixes to the concave face of the shell) is predominately shielded from the coating and receives an unacceptably thin deposition of carbon.

BRIEF DESCRIPTION OF THE DRAWINGS

Features and advantages of embodiments of the present invention will become apparent from the appended claims, the following detailed description of one or more example embodiments, and the corresponding figures, in which:

DETAILED DESCRIPTION

In the following description, numerous specific details are set forth. However, it is understood that embodiments of the invention may be practiced without these specific details. Well-known structures and techniques have not been shown in detail to avoid obscuring an understanding of this description. References to "one embodiment", "an embodiment", "example embodiment", "various embodiments" and the like indicate the embodiment(s) so described may include particular features, structures, or characteristics, but not every embodiment necessarily includes the particular features, structures, or characteristics. Further, some embodiments may have some, all, or none of the features described for other embodiments. Also, as used herein "first", "second", "third" describe a common object and indicate that different instances of like objects are being referred to. Such adjectives are not intended to imply the objects so described must be in a given sequence, either temporally, spatially, in ranking, or in any other manner. Also, the terms "coupled" and "connected," along with their derivatives, may be used. In particular embodiments, "connected" may be used to indicate that two or more elements are in direct physical or electrical contact with each other and "coupled" may mean that two or more elements co-operate or interact with each other, but they may or may not be in direct physical or electrical contact. Also, while similar or same numbers may be used to designate same or similar parts in different figures, doing so does not mean all figures including similar or same numbers constitute a single or same embodiment.

When parts or substrates are coated in a fluidized particle bed wherein decomposition of a vapor occurs, such coating is carried out in a heated enclosure through which there is an upward flow of gas (e.g., a stream of a mixture of an inert or diluent gas and the feed gas or vapor that is being decomposed). Gas flow rates are controlled so as to levitate the bed of minute particles which generally alternatively rise and fall in a somewhat toroidal flow path. The substrates being coated are of a size and shape such that they are levitated by the upward flowing gas stream and thus are essentially suspended within the bed wherein they randomly tumble. The bed is heated to a temperature at which the feed gas decomposes and deposits a thin film coating upon the substrates and the particles. A small fraction of the particles are usually regularly removed and replaced so as to maintain bed surface area at a generally constant level. When the substrate shapes are such that they tumble randomly within the fluidized bed, all of the surfaces thereof are fairly uniformly exposed to the flowing stream of gas, and as a result, have a substantially uniform thickness coating deposited thereupon. Because substrates of certain size (e.g., uneven weight distribution resulting in a "heavy" side and a "light" side) and shape (e.g., asymmetric) have a tendency to float within the bed in a substantially singular orientation (e.g., plum-bob or do not randomly tumble), then certain surfaces of such substrates are exposed directly to the upward flowing gas stream more than others, and the coating thickness deposited is no longer uniform.

However, by grouping multiple substrates to be coated by vapor deposition together as an assemblage, with the individual substrates disposed at regular spherical orientation one to another, the assemblage will be levitated within the coater with a regular tumbling movement. As a result, all of the surfaces of the substrates will randomly tumble and be exposed to about the same extent to the upwardly flowing gas stream, and the thickness of the coating deposited will be substantially uniform over the entire exposed surfaces of the substrates.

In an embodiment, non-uniform thickness coatings can be overcome by associating groups of such similar substrates and confining them so as to have a substantially fixed orientation spatially one to another; then, when the confined group is levitated in an upwardly flowing gas stream, high uniformity of coating thickness can be achieved. Excellent results are obtained when coating with pyrocarbon in a bed of fluidized particles.

An embodiment includes a method for coating multiple substrates in a fluidized bed of particles by depositing pyrocarbon thereupon in a manner to obtain uniform coating thickness across each coated substrate surface, which method comprises the steps of establishing a bed of particles in a fluidized condition in a coating zone within an enclosure, which particles are levitated by supplying an upward flow of a gaseous atmosphere (which may comprise an inert gas and/or a hydrocarbon and/or other gases), providing a group of substrates of generally similar shape and size to be coated, confining the group of substrates in association with each other so as to have a substantially fixed orientation spatially one to another, levitating the confined group of substrates within the fluidized particle bed so that the association of substrates tumbles randomly within the bed, and heating the fluidized bed to a temperature such that the hydrocarbon decomposes to deposit pyrocarbon, whereby surfaces of the substrates upon which pyrocarbon is being deposited are uniformly exposed to upward gas flow and, as a result, a coating of pyrocarbon of substantially uniform thickness is deposited upon the substrates throughout the surface area thereof.

An embodiment includes a method for coating multiple substrates in a fluidized bed of particles by vapor decomposition to deposit thereupon in a manner to obtain uniform thickness of coating, which method comprises the steps of establishing a bed of particles in a fluidized condition in a coating zone within an enclosure, which particles are levitated by supplying an upward flow of a gaseous atmosphere comprising gas (e.g., inert gas and a thermally decomposable vapor), providing a group of substrates of generally similar shape and size to be coated, confining the group of substrates in association with each other so as to have a substantially fixed orientation spatially one to another, levitating the confined group of substrates within the fluidized particle bed so that the association of substrates tumbles randomly within the bed, and heating the fluidized bed to a temperature such that the vapor decomposes to deposit a coating upon the substrate, whereby surfaces of the substrates are uniformly exposed to upward gas flow and, as a result, a coating of pyrocarbon of substantially uniform thickness is deposited upon the substrates throughout the surface area thereof.

An embodiment provides an assemblage for coating multiple substrates in an upwardly flowing gaseous stream so as to deposit a coating of uniform thickness across the coated surfaces, which assemblage comprises a group of substrates of generally similar shape and size to be coated, and a container or cage confining the group of substrates in association with each other so as to have a substantially fixed orientation spatially one to another, whereby the confined group of substrates can be levitated within a coater to which an upward flow of gaseous atmosphere is supplied wherein the assemblage will tumble randomly, as a result of which surfaces of the substrates are uniformly exposed to upward gas flow and have a coating of substantially uniform thickness deposited thereupon.

The operation of various embodiments is described herein with respect to a pyrocarbon coating process where a gaseous hydrocarbon is pyrolytically decomposed in a fluidized bed of minute particles. However, it should be understood that embodiments might be advantageously practiced with other vapor decomposition coating methods (e.g., methods where there is levitation of the substrates within an upwardly flowing gas stream containing a feed gas or vapor that will be chemically decomposed by the application of heat to deposit a coating on the surfaces of the levitated substrates). When pyrocarbon is the desired product, the coater may be a fluidized bed coater and upwardly flowing gas stream may be a mixture of feed gas in the form of propane or propylene, for example, and an inert gas such as argon, nitrogen or helium.

Figure 5:
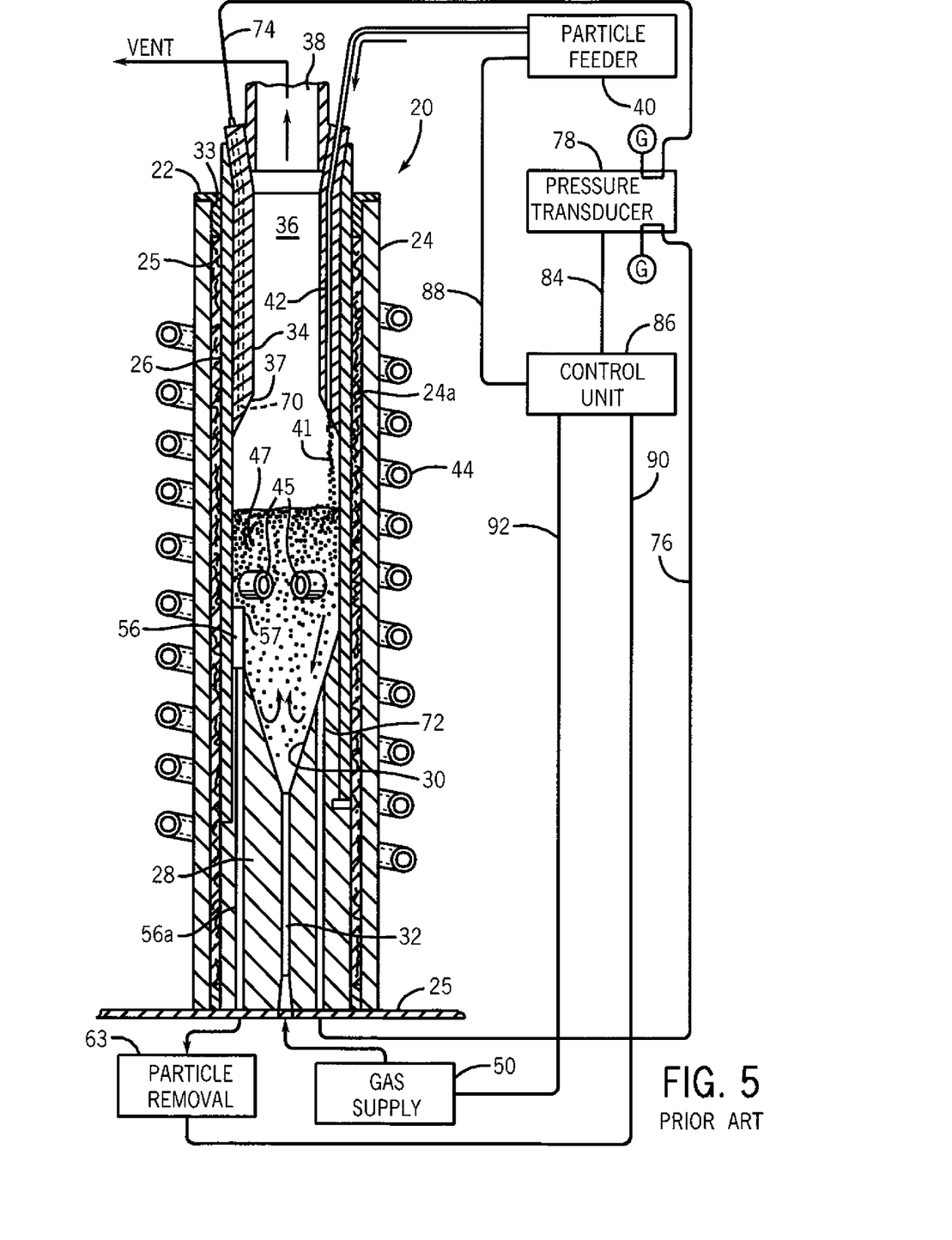
FIG. 5 is a schematic view, partially in section, of a prior art fluidized bed coater.

Illustrated in FIG. 5 is a conventional fluidized bed coating apparatus 20 which includes a furnace 22 having an outer cylindrical shell 24 within which a coating enclosure is located. Details of the construction and operation of the fluidized bed coating apparatus are set forth in U.S. Pat. No. 5,284,676, the disclosure of which is incorporated herein by reference. The furnace 22 is supported upon a water-cooled support plate 25 to which it may be bolted. A coating enclosure is generally separated from the outer cylindrical shell 24 by a layer of insulation 24a and is defined by an elongated sleeve 26 which fits about the upper end portion of a lower nozzle block 28 that has an interior conical bottom surface 30 which extends upward from a vertical central passageway 32 that is coaxial with the exterior of the nozzle block and the elongated tube 26, both of which are circular in cross-section. The upper end of the furnace includes an annular spacer 33, which centers the coating tube or sleeve 26, and an upper insert 34 that defines a central exit passageway 36. The insert 34 has a frustoconical bottom surface and several passageways in its thickened wall. The heated levitating and coating gases leaving the fluidized bed coater travel through this exit passageway 36 and through a suitable conduit 38 leading to an appropriate vent.

A particle feeder 40 is mounted generally above the fluidized bed coater 20 and is designed to feed minute particles 41 into the coating enclosure at a desired rate. The particles from the feeder 40 enter the coater through an entrance conduit provided by one of the passageways 42 in the wall of the insert. A suitable induction or alternating current heating device 44 is located in surrounding relationship to the furnace tube; it heats the active deposition region of the coating enclosure as well as the small particles and the objects being levitated to bring them to the desired temperature at which pyrolytic deposition occurs.

A coating operation is usually carried out by first establishing a levitated bed of minute particles of submillimeter size. This fluidized bed is maintained in a lower coating region 47 of the coating chamber as illustrated. Separate objects to be coated within the particles that comprise the bed, for example annular heart valve bodies 45 or orthopedic implants, machined from dense isotropic graphite or the like, are appropriately loaded into the bed through the upper exit passageway 36; they are then supported among the fluidized particles in the bed being levitated by the upwardly flowing gaseous stream. The temperature within the coating enclosure is appropriately monitored and controlled to heat the particles and the substrates to the desired temperature.

When the coating process is ready to begin, a carbonaceous substance, such as a gaseous hydrocarbon (e.g., propane, propylene, methane, etc. or a mixture thereof) is added to the fluidizing gas stream. The supply of the gaseous mixture is handled through flow-regulating valve arrangements that are part of a gas supply system 50 which operates to appropriately mix the hydrocarbon and the fluidizing gas. In the illustrated arrangement, the gas being supplied flows upward through the central passageway 32 and creates a generally toroidal flow pattern of particles within the coating enclosure; generally the particles and substrates flow upward in a central region of the bed and fan out at the top of the bed, returning along the interior cylindrical sidewall of the tube 26.

The primary object of such coating operation will usually be to coat the exterior surfaces of small substrates tumbling in the fluidized bed of supporting particles, with a uniform coating of pyrocarbon. The character of the bed may be constantly changing because the minute particles in the bed grow in size as a result of the coating that is occurring. For coating with pyrocarbon, an amount of small particles (e.g., spheroids) may be provided having sufficient total surface so that there will be, for example, at least about 70 sq. cm of surface for each cu. cm of volume in the active coating region. In an embodiment, such ancillary particles are about 1,500 microns or less in size with an average size not greater than about 800 microns. In order to maintain a desired, fairly constant bed character, a small amount of particles are generally continuously removed from the bed, and new particles (which may be substantially smaller in size) may be continuously added. Particle removal may be effected through an exit conduit 56 having an exit hole 57 in its side wall, and particles that enter this conduit fall by gravity through a passageway 56a in the nozzle block 28. They ultimately pass through a hole in the support plate 25 and enter a particle removal system 63 where they are collected and weighed. As previously indicated, they may be replaced with particles 41 of smaller size that are supplied by the particle feeder 40 and enter an upper region of the fluidized bed.

In the illustrated arrangement, the size of the fluidized bed within the coating enclosure may be regulated in order to precisely control the crystalline character of the pyrocarbon being deposited. Control may be effected by measuring the pressure differential across the fluidized bed by monitoring the pressure difference between a point at a lower region in the bed or below the bed and a point above the bed. To this end, an upper pressure-sensing port 70 is provided in the upper insert 34, and a lower pressure-sensing port 72 is provided at the end of a long passageway in the nozzle block 28. The upper port 70 and the lower port 72 may be respectively connected via tubing 74, 76 to a pressure transducer 78 for measuring the pressure at these ports and then comparing the two pressures measured to determine the difference therebetween. To keep the ports and tubing clear of dust, carbonaceous material and the like, an appropriate slow purge flow of inert gas may be maintained through both port systems. A signal from the pressure transducer 78 may be sent via line 84 to control unit 86, which instigates appropriate adjustments by sending signals to the particle removal system 63 and the particle feeder 40 through lines 88 and 90. The control unit 86 also controls the gas supply system 50, sending signals via a line 92.

Figure 1:
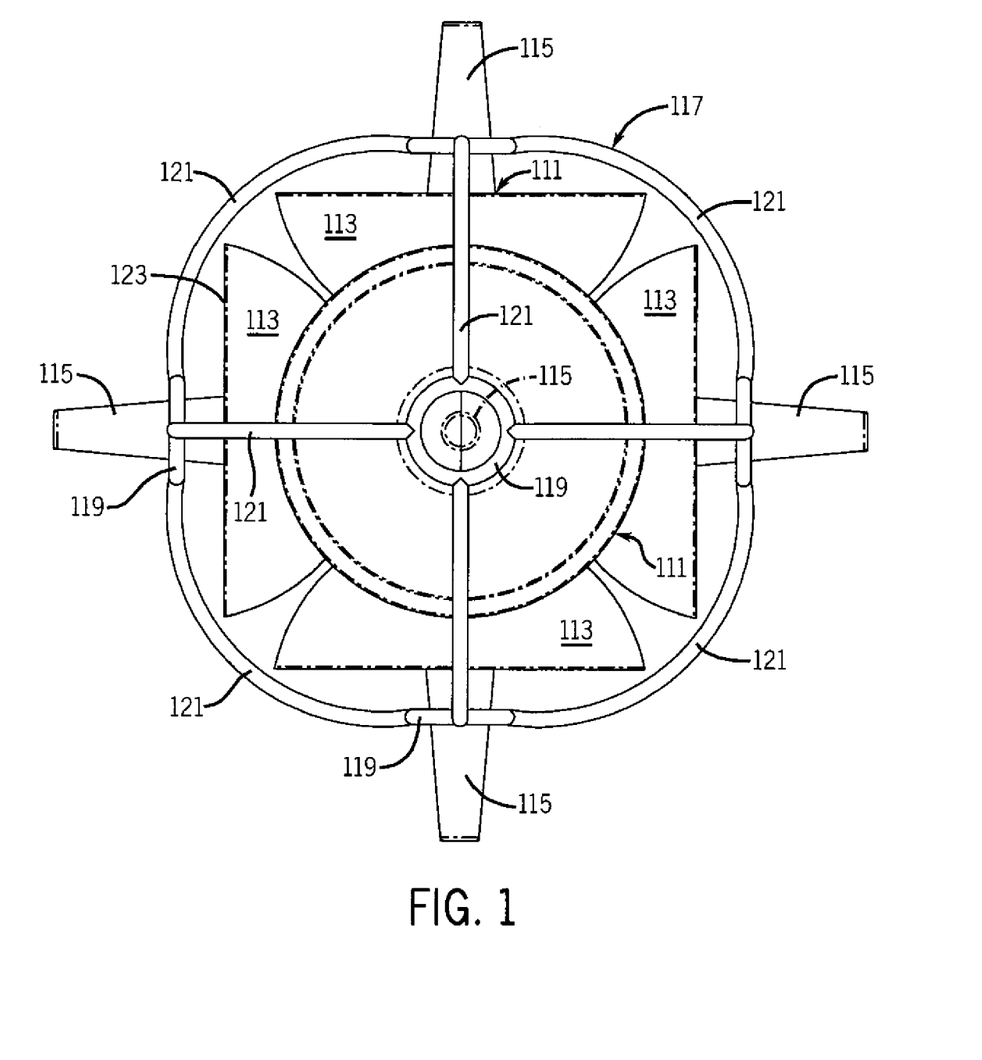
FIG. 1 is a front view of an assemblage of six substrates to be coated in a fluidized bed coating operation confined in spatial relation to one another by a surrounding holder.

Illustrated in FIG. 1 is an embodiment with an arrangement for coating small substrates 111, which are useful as orthopedic implants having the shape of a generally hemispherical shell or head 113 and a stem 115 that extend axially from a central region of the concave surface of the thin shell or head. Although the head 113 does not have the shape of a complete hemisphere, for convenience of description, it is referred to as hemispherical, even though its surface is only a segment or section of a sphere. In an embodiment, grouping six of these substrates 111 with their spherical convex surfaces juxtaposed with one another and their stems 115 disposed essentially in three planes that are each perpendicular to one another, may yield a uniform coating of the entire surfaces of the substrates 111 because the confined group of six substrates tumbles randomly within a fluidized bed coating region 47, such as exemplified in FIG. 5.

Maintenance of the six substrates 111 in this desired regular spatial orientation one to another is accomplished through the use of a confining cage or holder 117. In an embodiment, the cage 117 comprises six rings 119 that are regularly located as a part of a three-dimensional array, interconnected with one another by a total of twelve legs 121. The legs 121 each have an arcuate central portion and short straight end portions with each terminus thereof of fixed to one of the rings 119 at four equiangularly (i.e. 90 degrees) spaced apart locations on the ring. The cage 117 is proportioned so that the six substrates 111 are accommodated therewithin with the respective stem 115 of each protruding through one of the rings 119. The inner diameter of each ring 119 is sized so as to be slightly greater than the exterior diameter of the stem 115 at the respective location along the frustoconical surface thereof where the ring will surround it in the assemblage.

The overall arrangement is such that there will be no part of the cage that will be in constant contact with any point on the surface of the implant 111 being coated. In an embodiment, this arrangement of six regularly spatially oriented substrates will generally continuously tumble randomly within the fluidized bed of particles so there will be uniform exposure of the entire surfaces of the substrates to the upflowing stream of gas. In an embodiment, there will be slight movement of the six substrates 111 within the cage 117, but such movement will be limited. Axial movement of any one substrate in an inward direction will be halted by contact with, for example, one or more of the four spherical shells 113 that it faces, while the surrounding ring 119 loosely confines the frustoconical stem. Movement of the substrate 113 in the opposite axial direction would be met by its flat edge 123 contacting one or more of the four legs 121 at one or more of four points. The substrates 111 are free to rotate about their axes as the rings 119 are sized so as not to retard relative rotation of the stem 115 about its axis at any time. Such relative rotation will occur at the points where a substrate may contact the cage or another substrate. In this respect, the inner diameter of the ring 119 is designed in an embodiment so as to be larger by about 20-35%, or between about 25% and about 30% larger than the diameter of the location on the frustoconical stem 115 with which it will be aligned when the flat edge of the substrate 123 abuts the four confining legs 121.

Figure 2:
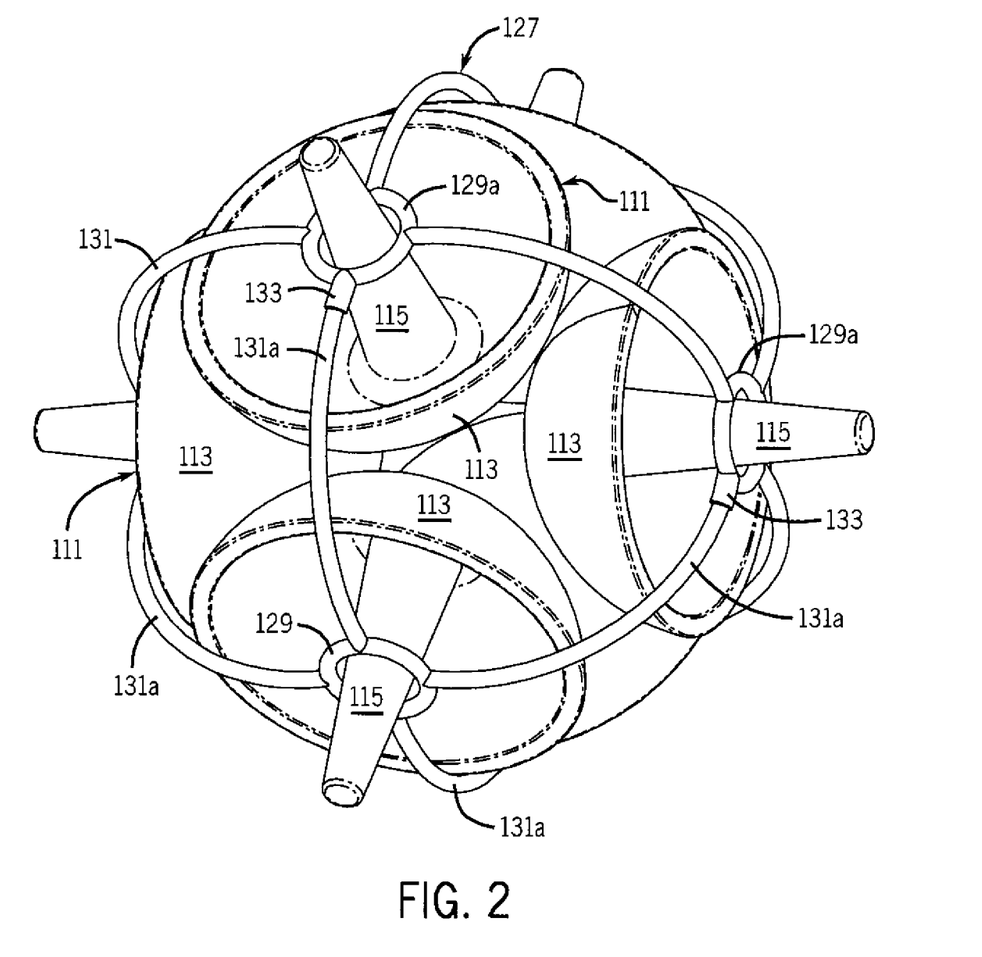
FIG. 2 is a perspective view of an assemblage of substrates, the same as those shown in FIG. 1, which are confined by a holder of slightly different shape.

Illustrated in FIG. 2 is an embodiment of a holder or cage 127 designed to confine six of the stemmed substrates 111 described above. The cage 127 also includes six rings 129 which are equidistantly located in three mutually perpendicular planes by twelve legs 131. Unlike holder 117, with holder 127 legs 131 are sections of a circle or ring having a constant radius of curvature. The result is a slightly more spherical-looking cage 127 as compared to the cage 117. As with the cage 117, cage 127 is proportioned so that each of the six substrates can shift and relatively rotate about its axis within the cage but cannot exit from the cage or assume a position where two or more of the substrates would bind against the cage and one another.

Cages 117, 127 can be fabricated from any suitable materials that will withstand the temperatures at which the vapor deposition processes will be carried out. With respect to pyrocarbon coating processes, temperatures are used within the range of about 1200° C. to about 2000° C. For example, when a mixture of 40% propane and 60% nitrogen is used, the operating temperature may be maintained at about 1400° C. As an example, a flow rate of about 20 liters per minute may be fed through a coater wherein the coating region has an interior diameter of about 3.5 inches. Molybdenum and tantalum alloys are examples of suitable materials for the fabrication of the cages. Although the cages may be formed of wire material of circular cross section, as illustrated in the drawings, they could be fabricated from various types of perforated, cut and/or bent sheet metal; alternatively, they could be cast or suitably machined.

A variety of arrangements may be used to facilitate the loading of a cage with the plurality of substrates (e.g., six stemmed implants). Illustrated in FIG. 2 is one arrangement that might be employed; instead of fastening four of the legs 131a directly to the rings 129a, a sleeve connector 133 is affixed to the ring 129a that will securely receive and hold the terminus of a leg 131a. Accordingly, with this type of arrangement, five of the substrates 111 can be loaded into the cage or holder 127, and then the sixth substrate with its stem 115 extending through the ring 129a can be mated to this by inserting the respective ends of the four legs 131a into the socket-type sleeves 133. Although not illustrated, a similar arrangement would work as well other embodiments such as cage 117.

When cage 127 with its six stemmed implants 111 is loaded into the coating furnace through the upper end, it becomes submerged in the fluidized bed and is levitated along with the particles that form the bed by the upflowing gaseous stream. The six substrates have their convex spherical surfaces in a regular spatial orientation facing one another, and their axes are all aimed generally at the center of the substantially spherical enclosure provided by the cage 127. As a result, the assemblage will tumble generally continuously and randomly while in the bed as the coating deposition progresses. The result is that all or substantially all of the surfaces of the stemmed substrates 111 are substantially equally exposed to the upflowing stream of gas, and are coated generally uniformly across their entire exposed surfaces.

Figure 3:
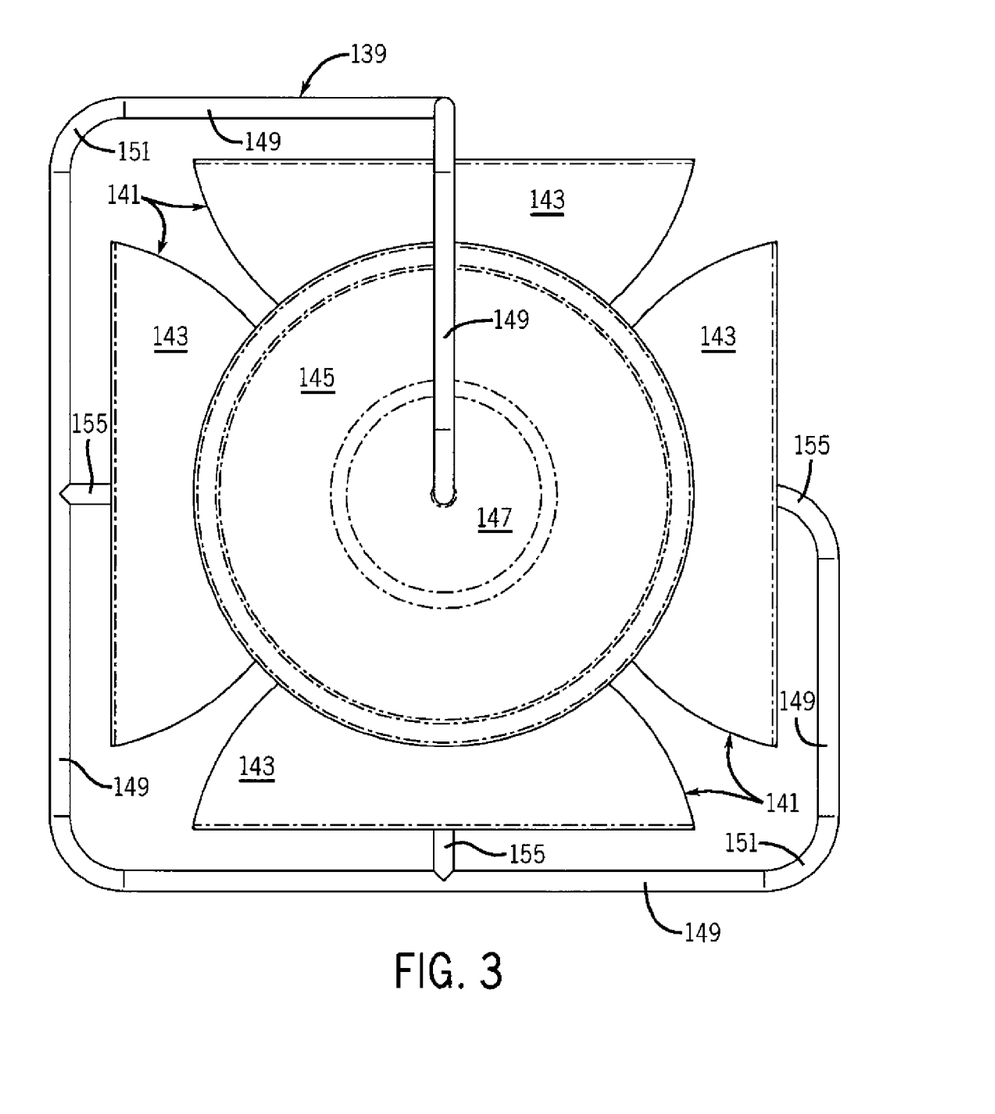
FIG. 3 is a view similar to FIG. 1, showing an assemblage of six thin hemispherical shell substrates, which are held in regular spatial orientation one to another by a holder of a different construction.
Figure 4:
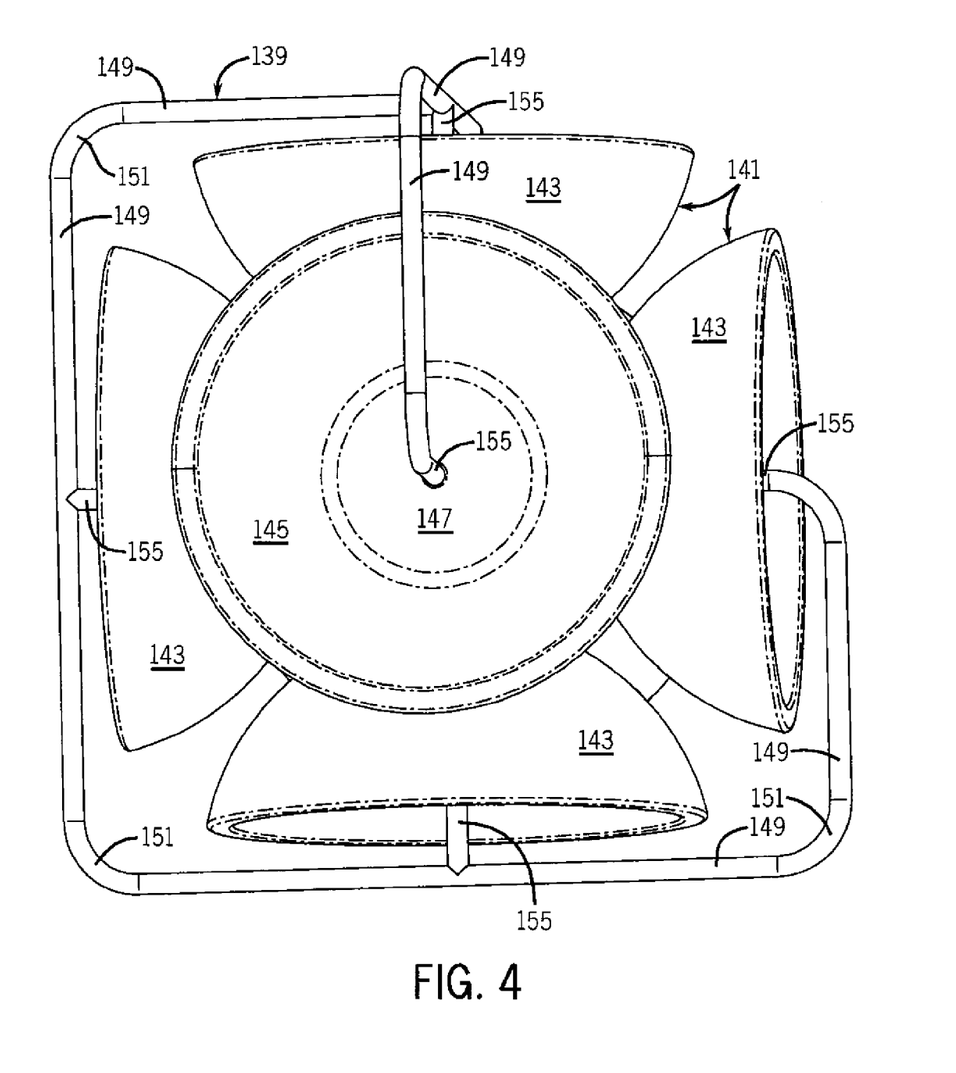
FIG. 4 is a perspective view of the assemblage shown in FIG. 3.

Illustrated in FIGS. 3 and 4 is another embodiment of a holder or a cage 139 that is designed to support six substrates 141 in a regular spatial orientation with respect to one another for coating in a fluidized bed via vapor decomposition. Substrates 141 are generally hemispherical hollow shells, each having a convex spherical surface 143 and a concave generally spherical surface 145 that extends outwardly from a small circular top wall 147.

Holder 139 comprises a surrounding framework which includes a plurality of straight sections 149 that lie generally along the surface of an imaginary cube. They are interconnected with one another at their ends by arcuate bends or elbows 151 so they lie at 90 degree angles to one another. This cubic framework supports six legs 155 which extend radially inward so that the six of them all point toward the center of the cubic framework. The legs 155 are proportioned in length so that they will each support one generally hemispherical shell substrate 141 at the desired interior location as shown in FIGS. 3 and 4.

Supporting interconnection between the tip of each leg 155 and the flat circular top wall section 147 of the substrate may be effected in any suitable manner desired. For example, substrate 141 could be provided with a short blind hole centrally of the flat top wall surface 147 into which the tip of the leg could be press fit. Alternatively, the tip of each leg 155 could be threaded, and a short hole with mating threads could be provided centrally of each circular flat top wall 147. As another alternative, the end of the leg might simply have a flat surface upon which a layer of adhesive could be provided that would be satisfactory to attach to the graphite substrate being coated and withstand the high temperatures of the pyrolytic deposition.

It should be apparent from FIGS. 3 and 4 that the six substrates can be serially attached to the six legs 155 so that they are spatially regularly oriented with their convex spherical surfaces pointing spherically toward one another. When such an assemblage, as shown in FIGS. 3 and 4, of six substrates 141 supported within the holder 139, is loaded into the coating furnace throughout the open upper end, it will again be submerged within the fluidized bed and will tumble continuously and randomly as it is levitated by the upflowing gas stream. As a result, the entire surfaces of each generally hemispherical shell substrate will be uniformly coated with pyrocarbon or with whatever coating is being deposited, to provide a uniform thickness. The only surface location that will not be coated would of course be the small area of contact between the leg and the top wall. However, if for example the substrate is an orthopedic implant, this location would not be an articular surface and thus less critical. Accordingly, the hole or other location within or upon what would likely be an isotropic graphite substrate might either be left as is or simply filled with a suitable biocompatible material.

Figure 6A:
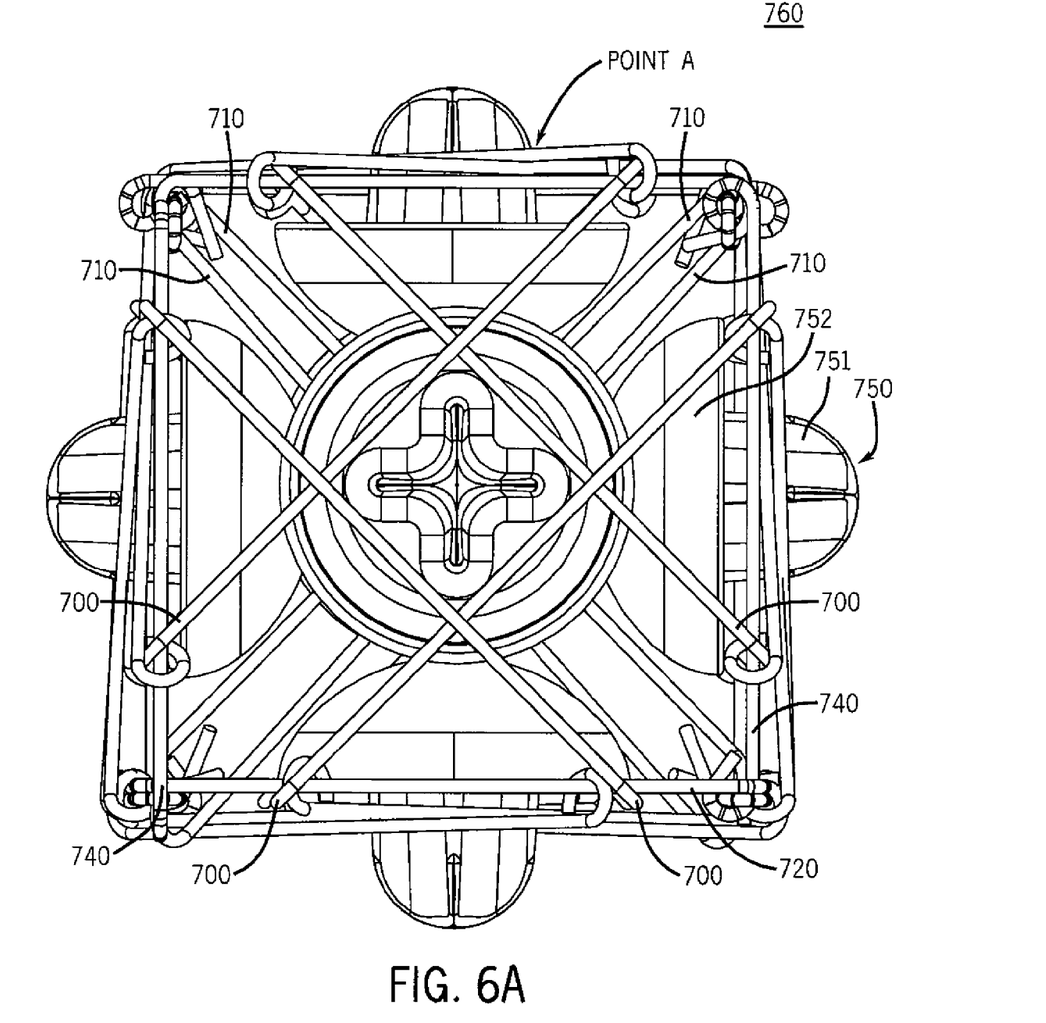
FIGS. 6A and 6B are side and perspective views of an embodiment of the invention.
Figure 6B:
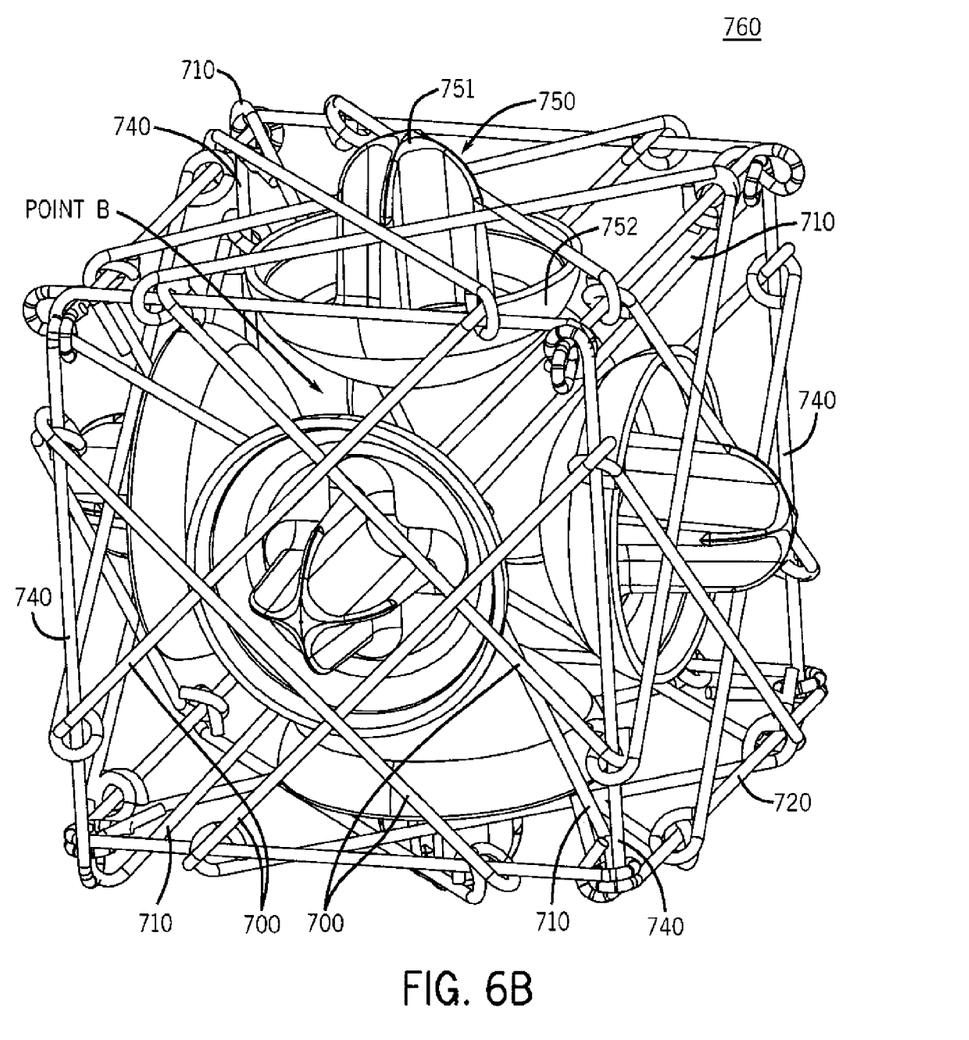
Figure 7A:
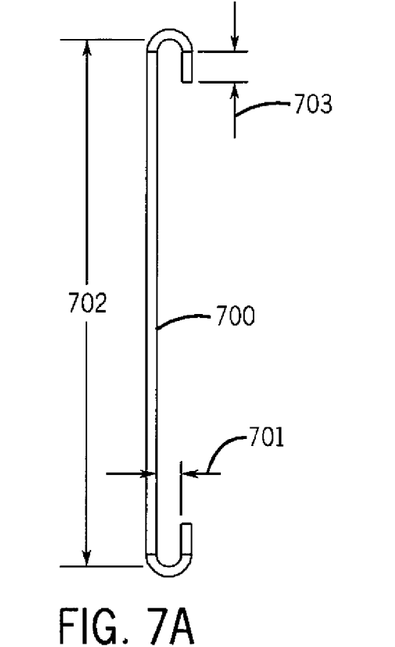
FIGS. 7A-E are side views of components of the embodiments of FIGS. 6A and 6B.
Figure 7B:
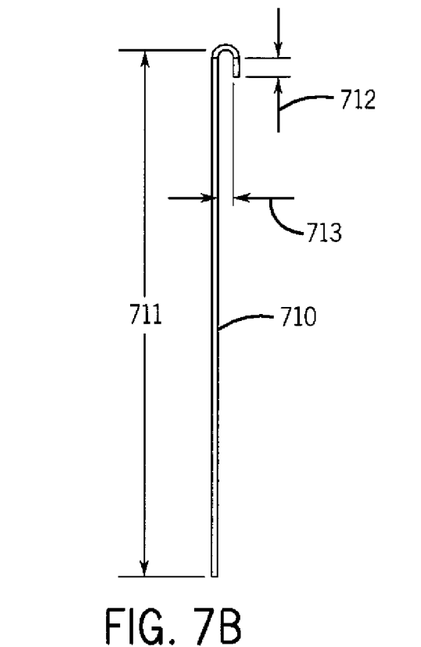
Figure 7C:
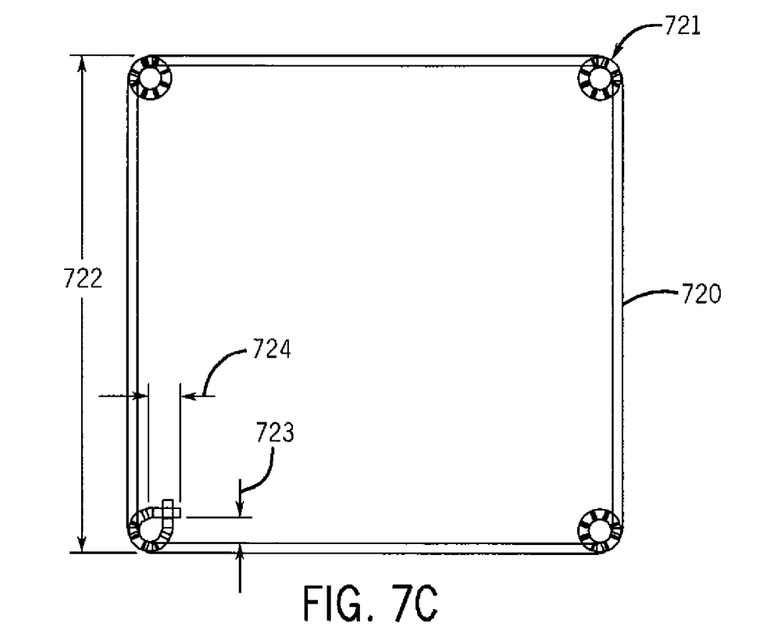
Figure 7D:
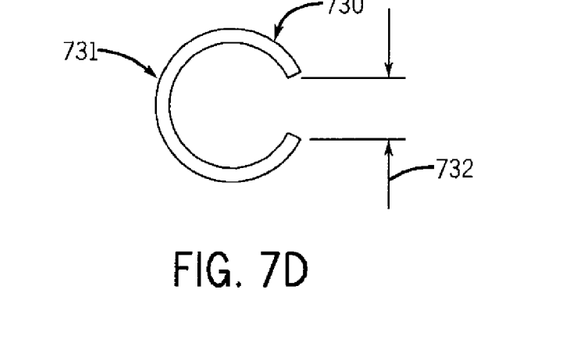
Figure 7E:
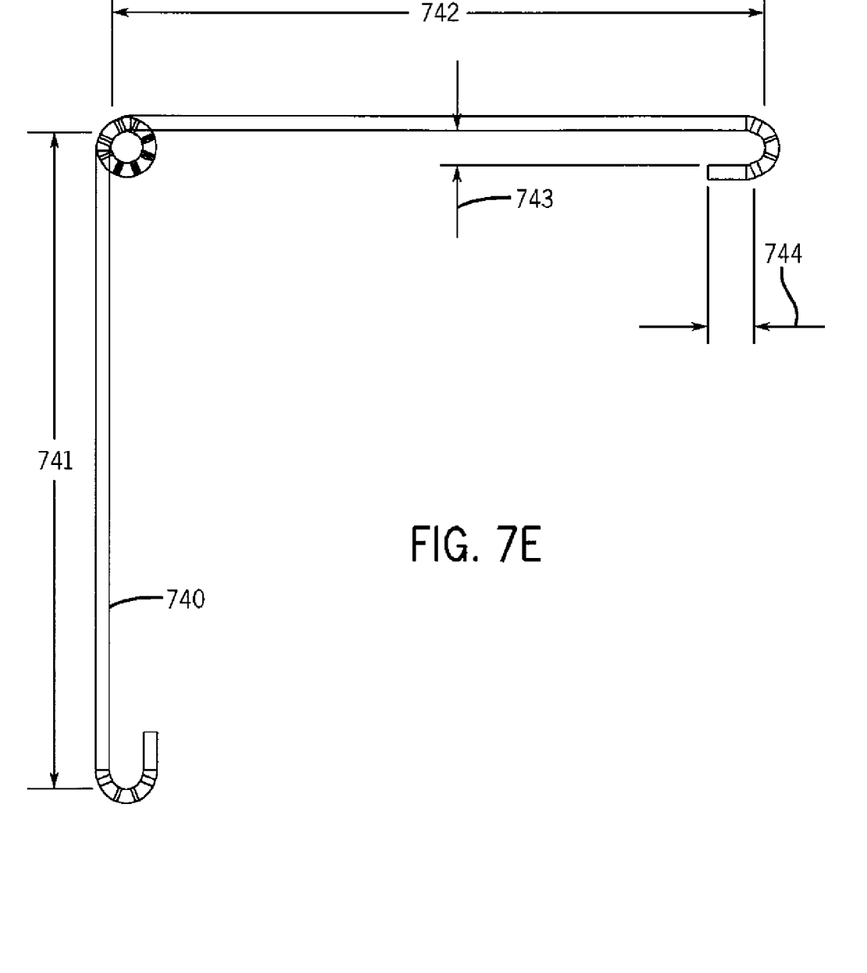

FIGS. 6A and 6B are side and perspective views of an embodiment of the invention. The figures are not meant to be assembly drawings and are merely illustrative of a general assemblage for providing even coatings (e.g., pyrocarbon) to substrates, such as biologic implants. Holder or cage 760 supports six substrates 750 in a regular spatial orientation with respect to one another for coating in a fluidized bed via vapor decomposition. Other embodiments may include more or less than six substrates while still providing regular orientation between substrates, which will avoid or lessen plumbbob orientations (and the consequent uneven coating).

In embodiments of FIGS. 6A-B, substrates 750 are generally hemispherical hollow shells, each having a spherical surface 752 that extends outwardly to stem 751. Holder 760 comprises a surrounding framework which includes main supports 740 (shaded in FIG. 6B), base 720, cross rods 710, circular piece 731, and tie rods 700 (see FIGS. 7A-E). Holder 760 may be made in numerous cage sizes to ensure differently sized parts can move inside cage enough to avoid constant contact with the cage (which can lead to the part fusing to the cage due to carbon coating) but not so lose as to inflict forces on the coating (due to excessive rattling) that might affect the structural integrity of the coating.

For example, the substrates are each confined such that spacing between any substrate 750 and any portion of cage 760 (e.g., as denoted by Point A of FIG. 6A) minimizes translation and/or rotation of the substrates during the entirety of the deposition process without resulting in constant contact for any of the substrates. Also, the substrates are each confined such that spacing between any two substrates 750 (e.g., as denoted by Point B of FIG. 6B) minimizes translation and/or rotation of the substrates during the entirety of the deposition process without resulting in constant contact for any of the substrates. In an embodiment, there is a maximum of 0.010 inches (e.g., during a collision while tumbling) to 0.500 inches (e.g., while substrates are in the cage but tumbling has yet to occur) of clearance between the substrate and a nearest cage member or other substrate. Thus, cage 760 allows each substrate to "jiggle" or move about during the random tumbling no more than 0.010 to 0.500 inches in any direction. These ranges may ensure parts can move enough to avoid constant contact with the cage but not so lose as to inflict forces on the coating that might affect the structural integrity of the coating.

Cage 760 is a cage embodiment that includes four main supports 740, one base 720, four cross rods 710, and twenty-four tie rods 700. Each cage member may be, for example, made from 0.050" diameter molybdenum. However, other embodiments are not so limited. Cage 760 is assembled by first using base 720 and four main supports 740 to assemble an outer cube. Next, four cross rods 710 are respectively attached to opposite corners of the cube, thereby extending across the middle portion (i.e., central core) of the cube. Circular piece 730 is attached at the intersection of cross rods 710 to tie them together in the center of the cube. Afterwards, a single tie rod 700 is attached diagonally across one face of the cube. Substrate 750 is then placed in the compartment with stem 751 pointing outwards from the cube (of course other orientations are possible such as the stem pointing inwards). Another tie rod 700 is then attached parallel to the first tie rod, also extending across the same face of the cube. A third tie rod 700 is then attached 90 degrees to the first two tie rods and across the same face of the cube. Next a fourth tie rod 700 is attached parallel to the third one and on the same face of the cube. Now the stem is "boxed" in by four tie rods 700. The above steps are then repeated for the remaining five sides of the cube to finally encompass six substrates. In an embodiment, the spacing between any substrate 750 and any tie rod can be adjusted by slightly pulling or bending the on the tie rod. The different members can be attached to one another by bending the ends about one another. When a cage 760 is loaded into the coating furnace the cage will be submerged within the fluidized bed and will tumble substantially continuously and randomly as it is levitated by the upflowing gas stream. As a result, generally all the surfaces of each implant will be substantially uniformly coated with pyrocarbon or with whatever coating is being deposited, to provide a uniform thickness.

Thus, an embodiment includes a method of coating substrates with a uniform thickness of coating (and/or a cage for doing the same). The method includes (a) supplying a flow of a gaseous atmosphere (which includes a thermally decomposable vapor) to form a fluidized bed (which may or may not include particles in addition to substrates to be coated); (b) providing substrates (e.g., implants) with each substrate having a similar asymmetrical shape (e.g., a shell with or without a stem); (c) confining the substrates, in a container, in a generally static orientation with one another (i.e., where some substrate movement is allowed but in general the substrates maintain a consistent orientation with one another such as would be the case with, for example, FIGS. 6A-B). The asymmetrical shape is one that would plum-bob if it were not confined in the container. The substrates would be collectively positioned evenly about a central core of the container. The central core may be defined as a spatially central portion of the container, a center of gravity for the container, and the like. For example, two adjacent substrates may not be positioned symmetrically about a core of the container but two opposite substrates would be. By "collectively" the entirety of the substrates in the container would be symmetrically and evenly spaced and oriented about the core so as to provide random tumbling and avoid plum-bobbing. The method may then include randomly tumbling the container of substrates within the fluidized bed based on the symmetrical orientation of the substrates within the container. The container may be configured to allow each substrate to: (i) pivot about an axis (e.g., long axis extending along stem 751) of the substrate, and (ii) jiggle (i.e., move about) during the random tumbling so the substrate is not in constant contact with any other substrate or any portion of the container (to avoid fusing the substrate to another substrate or the container with the coating). The randomly tumbling will then help provide a coating of generally uniform thickness on generally all portions of each substrate. Of course each substrate may have geometrical conditions that preclude absolute even coating (e.g., a deep channel that is difficult for vapor to penetrate) but such uneven coating would not be due to a plum-bob effect. The method may have two substrates oppositely oriented about a line of symmetry to each other. For example, such a situation is met by two substrates in FIG. 6A whose stems are parallel to each other but pointing in opposite directions. In an embodiment, the substrates each include a shell portion 752 having convex and concave surfaces.

Again, cage 760 may be made in a variety of sizes. In various embodiments, various ranges of dimensions (inches) are as follows: 701 (0.7, 0.8, 0.9, 1.0, 1.1, 1.2, 1.3, 1.4); 702 (2.25, 2.50, 2.75, 3.00, 3.25, 3.50); 703 (0.09, 0.10, 0.11, 0.12, 0.13, 0.14, 0.15, 0.16); 711 (3.5, 4.0, 4.5, 5.0, 5.5, 6.0); 713 (0.09, 0.10, 0.11, 0.12, 0.13, 0.14, 0.15, 0.16); 712 (0.11, 0.12, 0.13, 0.14, 0.15, 0.16, 0.17, 0.18); 741 and 742 (2.0, 2.1, 2.2, 2.3, 2.4, 2.5, 2.6, 2.7, 2.8, 2.9); 743 (0.09, 0.10, 0.11, 0.12, 0.13, 0.14, 0.15, 0.16); 744 (0.11, 0.12, 0.13, 0.14, 0.15, 0.16, 0.17, 0.18); 721 and 723 (0.09, 0.10, 0.11, 0.12, 0.13, 0.14, 0.15, 0.16); 724 (0.11, 0.12, 0.13, 0.14, 0.15, 0.16, 0.17, 0.18); 722 (2.0, 2.1, 2.2, 2.3, 2.4, 2.5, 2.6, 2.7, 2.8, 2.9); 732 (0.15, 0.17, 0.19, 0.21, 0.23, 0.25); and 731 (0.3, 0.4, 0.5, 0.6, 0.7).

Although various embodiments of the invention have been described, it should be understood that various changes and modifications as would be obvious to one having ordinary skill in this art may be made without departing from the scope of the invention. For example, although the substrates which comprise generally hemispherical hollow shells have been shown (e.g., which are suitable for prospective orthopedic implants such as shoulder implants), other types of substrates (e.g., finger implants, hip implants, heart valves, other cardiovascular implants, and the like) that might not individually tumble regularly within a fluidized bed coater can be supported in a regular spatial orientation one to another in a cage or by a holder in order to provide an assemblage that will tumble continuously and randomly and thus assure a generally uniform coating across the exterior surfaces thereof. Although fluidized pyrocarbon coating methods are described and illustrated, other chemical vapor deposition methods (e.g., using precursor feed gas diluted in a carrier or diluent that is flowed upwardly to contact a levitated and heated substrate) may be employed to deposit coatings (e.g., Ti, Ta, W, Si from suitable halides, hydrides and the like) on substrates. It is intended that the appended claims cover all such modifications and variations as fall within the true spirit and scope of this present invention.

What is claimed is:

1. A method for coating multiple substrates in a fluidized bed of particles by depositing pyrocarbon thereupon in a manner to obtain uniform coating thickness across the each coated substrate surface, which method comprises the steps of:
- establishing a bed of particles in a fluidized condition in a coating zone within an enclosure, which particles are levitated by supplying an upward flow of a gaseous atmosphere comprising a hydrocarbon,
- providing a group of substrates of generally similar shape and size to be coated,
- confining the group of substrates in association with each other so as to have a substantially fixed orientation spatially one to another,
- levitating the confined group of substrates within the fluidized particle bed so that the association of substrates tumbles randomly within the bed,
- heating the fluidized bed to a temperature such that the hydrocarbon decomposes to deposit pyrocarbon on the group of substrates,
- uniformly exposing surfaces of the substrates, upon which pyrocarbon is being deposited, to the upward gas flow, and
- depositing a coating of pyrocarbon of substantially uniform thickness throughout the surface areas of the surfaces of the substrates.

2. The method according to claim 1 wherein the group of substrates comprises at least two substrates oppositely oriented, about a line of symmetry, to each other.

3. The method according to claim 1 wherein the group of substrates are confined with a regular orientation to one another so as to provide a view that is substantially the same when viewed in any one of three perpendicular planes.

4. The method according to claim 1 wherein the substrates each include a shell portion having convex and concave surfaces.

5. The method according to claim 4 wherein the convex and concave surfaces are sections of spherical surfaces.

6. The method according to claim 1 wherein the confining is effected in a manner in which no surface of any substrate is in constant contact with a confining fixture.

7. The method according to claim 1 wherein the substrates are confined by attachment at a single location to a fixture that secures them in rigid orientation one to another.

8. A method of coating substrates with a uniform thickness of coating comprising:
- supplying a flow of a gaseous atmosphere, which includes a thermally decomposable vapor, to form a fluidized bed;
- providing substrates each having a similar asymmetrical shape;
- confining the substrates, in a container, in a generally static orientation with one another such that the substrates are collectively positioned evenly about a central core of the container;
- randomly tumbling the container of substrates within the fluidized bed based on the generally static orientation of the substrates in the container, wherein the container allows each substrate to: (a) pivot about an axis of the respective substrate, and (b) jiggle during the random tumbling so the respective substrate is not in constant contact with any other substrate or any portion of the container; and
- providing a coating of generally uniform thickness on generally all portions of each substrate based on the random tumbling.

9. The method according to claim 8 wherein the substrates comprise two substrates oppositely oriented, about a line of symmetry, to each other.

10. The method according to claim 8 wherein the substrates are confined in the generally static orientation so as to provide a view that is substantially the same when viewed in any one of three perpendicular planes.

11. The method according to claim 8 wherein the substrates each include a shell portion having convex and concave surfaces.

12. The method according to claim 11 wherein the substrates are one of orthopedic and cardiovascular implants.

13. The method according to claim 8 wherein the container allows each substrate to jiggle during the random tumbling no more than 0.6 inches in any direction.

14. The method according to claim 8 wherein each substrate is configured to plum-bob within the fluidized bed, if not confined in the container, based on the asymmetrical shape of the respective substrate.

* * * * *